US012778908B2

(12) United States Patent
Glover et al.

(10) Patent No.: US 12,778,908 B2
(45) Date of Patent: Nov. 3, 2026

(54) METHOD OF PREPARING A TOPICAL PHARMACEUTICAL COMPOSITION

(71) Applicant: PHEBRA PTY LTD, Lane Cove West (AU)

(72) Inventors: William John Glover, Lane Cove West (AU); Alexander Malvin Eutick, Lane Cove West (AU)

(73) Assignee: PHEBRA PTY LTD, Lane Cove West (AU)

( * ) Notice: Subject to any disclaimer, the term of this patent is extended or adjusted under 35 U.S.C. 154(b) by 551 days.

(21) Appl. No.: 18/264,726

(22) PCT Filed: Feb. 9, 2021

(86) PCT No.: PCT/AU2021/050106

§ 371 (c)(1),
(2) Date: Aug. 8, 2023

(87) PCT Pub. No.: WO2022/170379

PCT Pub. Date: Aug. 18, 2022

(65) Prior Publication Data

US 2024/0099995 A1 Mar. 28, 2024

(51) Int. Cl.

| | |
|---|---|
| ***A61K 31/137*** | (2006.01) |
| ***A61K 9/00*** | (2006.01) |
| ***A61K 9/06*** | (2006.01) |
| ***A61K 31/167*** | (2006.01) |
| ***A61K 31/245*** | (2006.01) |
| ***A61K 47/02*** | (2006.01) |
| ***A61K 47/38*** | (2006.01) |

(52) U.S. Cl.

CPC .......... *A61K 31/137* (2013.01); *A61K 9/0014* (2013.01); *A61K 9/06* (2013.01); *A61K 31/167* (2013.01); *A61K 31/245* (2013.01); *A61K 47/02* (2013.01); *A61K 47/38* (2013.01)

(58) Field of Classification Search

CPC ..... A61K 9/0014; A61K 47/38; A61K 31/137

See application file for complete search history.

(56) References Cited

U.S. PATENT DOCUMENTS

| | | | | |
|---|---|---|---|---|
| 2005/0228336 A1 | | 10/2005 | Keusch et al. | |
| 2008/0085245 A1 | * | 4/2008 | Sheil ....................... | A61P 23/00 424/10.1 |
| 2013/0208560 A1 | | 8/2013 | Kulkarni et al. | |
| 2019/0290602 A1 | | 9/2019 | Akasapu et al. | |

FOREIGN PATENT DOCUMENTS

| | | | | | |
|---|---|---|---|---|---|
| CN | 102793691 A | | 11/2012 | | |
| EP | 0812587 A1 | | 12/1997 | | |
| JP | 2005-319288 A | | 11/2005 | | |
| WO | 2014/145767 A1 | | 9/2014 | | |
| WO | 2016/029214 A1 | | 2/2016 | | |
| WO | WO-2019162892 A1 | * | 8/2019 | .............. | A61K 9/08 |
| WO | 2020/237295 A1 | | 12/2020 | | |

OTHER PUBLICATIONS

Phebra Pty Ltd, Product Information: "Laceraine® Gel Topical Wound Anaesthetic—Lidocaine (Lignocaine) Hydrochloride Monohydrate, Tetracaine (Amethocaine) Hydrochloride and Adrenaline (Ephinephrine) Acid Tartrate" (Aug. 2020).

Phebra Pty Ltd, Australian Product Information: "Laceraine® Gel Topical Wound Anaesthetic," Version 1 (Aug. 2020).

Phebra Pty Ltd., New Product Announcement to Austin Hospital: "Laceraine® Gel Topical Wound Anaesthetic—Phebra Code SOL053" (letter dated Aug. 3, 2020—letter sent Aug. 5, 2020).

Phebra Pty Ltd., New Product Announcement to Prince of Wales Hospital / Sydney Children's Hospital: "Laceraine® Gel Topical Wound Anaesthetic - Phebra Code SOL053" (letter dated Aug. 3, 2020—letter sent Aug. 5, 2020).

Phebra Pty Ltd., New Product Announcement to Royal North Shore Hospital: "Laceraine® Gel Topical Wound Anaesthetic—Phebra Code SOL053" (Aug. 26, 2020).

Phebra Pty Ltd., New Product Announcement to Westmead Childrens Hospital: "Laceraine® Gel Topical Wound Anaesthetic—Phebra Code SOL053" (Dec. 8, 2020).

Phebra Pty Ltd, "Improving Safe Medication Delivery of Topical Wound Anesthetic," 2020 *SCHN Quality and Innovation Awards,* General Entry Submission (submitted on Oct. 23, 2020—awards ceremony held on Nov. 26, 2020).

Phebra Pty Ltd., List of Hospitals and Other Entities to Which Product (Laceraine® Gel Topical Wound Anaesthetic) Was Provided Prior to Feb. 9, 2021.

Australian Patent Office, International Search Report in International Patent Application No. PCT/AU2021/050106 (Apr. 21, 2021).

Zanon et al., "Stability of a Novel Lidocaine, Adrenaline and Tetracaine Sterile Thermosensitive Gel: A Ready-to-Use Formulation," Eur. J. Pharm. Sci., 136: 104962 (2019).

European Patent Office, Extended European Search Report in European Patent Application No. 21925199.6 (Nov. 13, 2024).

Japan Patent Office, Office Action in Japanese Patent Application No. 2023-548777 (Mar. 25, 2025).

* cited by examiner

*Primary Examiner* — Theodore R. Howell

(74) *Attorney, Agent, or Firm* — Leydig, Voit & Mayer, Ltd.

(57) ABSTRACT

The present invention relates to a method of preparing a topical pharmaceutical composition, a pharmaceutical composition prepared by the method, a topical pharmaceutical composition, and to uses and methods involving the pharmaceutical composition. The pharmaceutical composition comprises at least one local anesthetic agent and a vasoconstrictive agent. The method of preparing the composition comprises stirring an aqueous liquid comprising at least one local anesthetic agent and a vasoconstrictive agent, wherein the stirring is performed substantially without forming a vortex and under an inert gas. The at least one local anesthetic agent may be lignocaine and tetracaine, and the vasoconstrictive agent may be adrenaline.

18 Claims, 1 Drawing Sheet

METHOD OF PREPARING A TOPICAL PHARMACEUTICAL COMPOSITION

TECHNICAL FIELD

The present invention relates to a method of preparing a topical pharmaceutical composition. The composition comprises at least one local anesthetic agent, and a vasoconstrictive agent. The invention also relates to a topical pharmaceutical composition prepared by the method and to use of the composition, for example in reducing blood loss and anesthetizing a topical area of a subject, for example broken skin.

BACKGROUND ART

It will be clearly understood that, if a prior art publication is referred to herein, this reference does not constitute an admission that the publication forms part of the common general knowledge in the art in Australia or in any other country.

Topical local anesthesia is important in situations where pain needs to be controlled during minor operative procedures, especially in emergency situations where the patient is also bleeding, for example due to rashes, cuts or lacerations. This is important for allowing rapid and appropriate suturing and pain control treatment, especially for children where minor lacerations are extremely common.

For example, when a patient is bleeding and presents at an Emergency Department, treatment should be undertaken in a way that allows for the optimum functional or cosmetic result, with the least distress to the patient (especially when the patient is a child). When a patient is distressed during treatment, this can adversely affect treatment outcomes. For example, it can be very difficult to best treat a child who is uncooperative or terrified. Aside from the pain the patient may be in, blood loss around the wound can also result in significant anxiety for the patient, and excessive blood loss can also make treatment more complex.

Consequently, there is a need for pharmaceutical compositions that can both provide local analgesia, and also reduce blood loss. Furthermore, successful treatment outcomes may be enhanced if doctors and other medical practitioners are able to administer suitable pharmaceutical compositions safely and rapidly, without use of complex administration or formulation procedures. For this reason, when treating such wounds local anesthetic agents which can be applied directly to the wound are typically preferred.

In some cases, whether or not a pharmaceutical composition is appropriate for use on a wound or broken skin may be determined by the nature of the pharmaceutical composition or formulation, rather than the nature of the active agent(s). For example, lignocaine has been used as a local anesthetic for more than 50 years. There are pharmaceutical compositions comprising lignocaine that are inappropriate for use on broken skin due to factors such as the sterility of the composition, the potential for infiltration or systemic toxicity and the presence of preservatives. However, lignocaine is also used in compositions that are specifically designed for use on broken skin.

One combination of pharmaceutical agents that is used on broken skin is LAT (also known as LET or ALA). This combination includes lignocaine, adrenaline (epinephrine) and tetracaine (amethocaine) and may be sold in either gel or in solution form. However, despite the use of compositions comprising this combination of active agents for around 30 years, a difficulty for emergency personnel is that there has not been any commercial and approved product containing the actives. Consequently, the combination of active agents is compounded by pharmacists immediately before use, with the attendant risk of contamination, unknown or variable concentrations of the active agents (especially if they were compounded from existing drug formulations), and unknown stability of the solution (for example due to the temperature of prior storage, and exposure to light or the dilution of any antioxidants present). Furthermore, if the composition is to be prepared in sterile form (for example for use on broken skin), methods involving sterilization of the solution or gel may result in degradation of the active agents during the preparation process, or incomplete sterilization (rendering the composition unsuitable for use, but this may not even be detected).

It has been noted that the sterility assurance level (SAL) of preparations compounded by an aseptic process is, at best, several orders of magnitude lower than the SAL of terminally sterilized pharmaceutical products manufactured under Good Manufacturing Practices (GMPs) (Gudeman et al). Issues with manufacture, as well as problems due to a composition "running off" the skin can also make it difficult to determine how much active agents are actually applied to a particular wound.

Furthermore, it has been reported that serious problems associated with compounding mixtures of local anesthetics include that these commonly have no regulatory guidelines and typically contain higher concentrations of anesthetics than those found in formulations approved by the US Food and Drug Administration (FDA), and the same product prepared by independent compounding pharmacies may be inconsistent (Berkman et al.). Indeed, since 2003 the Missouri Board of Pharmacy has conducted a random testing program of extemporaneously prepared products from community pharmacies, and has found that of nearly 900 tested medicines, 22% have failed to be within the limits of ±10% for the active ingredient (which is the limit commonly required for US Pharmacopoeia formulations) (Australian National Coordinating Committee on Therapeutic Goods, 2008). Serious adverse effects that have been reported in association with compounded topical anesthetics include arrythmia, seizures, coma, methemoglobinemia and hypoxemia. The US FDA has cautioned against factors such as using too much agent, covering too much body surface area and applying to irritated or broken skin (Fry et al; Kennedy et al.; Wolf et al.).

LAT has needed to be compounded by pharmacies due to issues with the stability of the product. For example, it has been necessary to store LAT at low temperatures (for example 0-4° C.) and LAT is photosensitive. However, there can be difficulties for compounding pharmacies to appropriately dissolve a gelling agent (if the composition is to be formulated as a gel), and difficulties in ensuring appropriate concentrations of the active agents, not to mention difficulties in providing sterile compositions. There may also be difficulties for pharmacists if compounding instructions are not sufficiently clear. To the inventors' knowledge, there are no compositions comprising lignocaine, adrenaline and tetracaine which have been authorized by a regulatory body.

In various aspects, there is therefore a need to be able to prepare a pharmaceutical composition that is able to topically treat wounds for both blood loss and pain. In another embodiment, there is a need to be able to prepare a pharmaceutical composition that can be produced industrially, that is storage stable, and which can be prepared in a sterile manner.

SUMMARY OF INVENTION

In one aspect, the present invention is directed to a method of preparing a topical pharmaceutical composition, which may at least partially overcome at least one of the abovementioned disadvantages or provide the consumer with a useful or commercial choice. With the foregoing in view, the present invention in one form, resides broadly in a method of preparing a topical pharmaceutical composition, wherein the topical pharmaceutical composition comprises at least one local anesthetic agent, and a vasoconstrictive agent.

In a first aspect, the present invention provides a method of preparing a topical pharmaceutical composition, the method comprising stirring an aqueous liquid comprising at least one local anesthetic agent and a vasoconstrictive agent, wherein the stirring is performed substantially without forming a vortex and under an inert gas.

When the vasoconstrictive agent is adrenaline, the stability of adrenaline can pose major problems in providing a stable composition. Adrenaline is sensitive to oxidation during and after manufacture, and may be degraded due to poor sterilizing conditions. This is the primary reason that once made, LAT compositions are typically stored at 0-8° C. Even small amounts of oxygen are able to reduce the stability of LAT compositions. For example, both the British and US Pharmacopeia set wide limits on the concentration of adrenaline in combination formulations to allow for expected degradation, and in some cases the amount of adrenaline can be up to ±12.5% or even ±15%. By comparison, the common universal levels set for the release of individual drugs in final dose form is typically ±5%.

Key factors affecting the stability of adrenaline include pH, oxidation from exposure to oxygen (which may be enhanced by metals present in solutions) and light. Tetracaine, for example, is also affected by the same factors while lignocaine is not. Chemically, the catechol substructure of adrenaline appears to be primarily responsible for adrenaline's propensity to oxidize.

While combinations including adrenaline may have some stability if stored at lower temperatures, dramatic decreases in the concentration of adrenaline may be observed if compositions are stored at higher temperatures. For example, it was found that adrenaline can be stable for at least 28 days under both acidic and basic conditions when stored in a freezer, but at higher temperatures (4° C. and above) concentration loss of 100% was observed after 2 days, or within 90 minutes at 22° C. (Palazzolo et al).

Despite the stability factors associated with adrenaline being well known, to the inventors' knowledge no group has managed to stabilize a LAT combination for room temperature storage.

The inventors have advantageously found that a method which controls oxygen ingress is important to formation of a stable composition. The inventors have advantageously found that stirring the aqueous liquid comprising at least one local anesthetic agent and a vasoconstrictive agent under an inert gas is important to decrease the likelihood that oxygen enters into the liquid. However, stirring the liquid substantially without forming a vortex is also important, as when a vortex forms matter (including gases) in the space above the vortex become drawn into the liquid. Consequently, if a vortex forms during stirring there is a much higher likelihood that oxygen may enter the liquid.

As used herein, the term "inert gas" relates to a gas that would not react with the at least one local anesthetic agent and the vasoconstrictive agent. Exemplary inert gases may include nitrogen, or a noble gas. The noble gas may be selected from the group consisting of helium, neon, argon, krypton, xenon and radon; especially helium, neon or argon; more especially argon. In one embodiment, the inert gas is nitrogen or argon; especially nitrogen.

The stirring in the first aspect may be under an inert gas in any suitable way. For example, the step of stirring may comprise flowing the inert gas over the surface of the aqueous liquid. A suitable rate of flow of the inert gas may be selected by a skilled person. In another embodiment, the step of stirring may comprise positioning the liquid in a closed container and displacing gas in the closed container with the inert gas. For the avoidance of doubt, in a closed container there may be gaps, for example in the lid, where inert gas and residual oxygen may escape. In one embodiment, the flow rate of inert gas is from 0.5% to 100% of the container volume per minute, especially from 0.5% to 80% or from 0.5% to 60% or from 0.5% to 40% or from 0.5% to 30% or from 1% to 20% or from 2% to 10% of the container volume per minute.

In the method of the first aspect the stirring is performed substantially without forming a vortex. When a liquid is stirred, the liquid flow may revolve around an axis (this may be coaxial with the rotation of a stirrer or impellor for example). The axis may be vertical, although it may also be oblique. A vortex is considered to form when the surface level of the liquid at the axis is significantly lower than the surface level of the surrounding liquid. In one embodiment, the stirring being performed substantially without forming a vortex is when the surface level at the axis of liquid revolution is less than 5 cm lower than the surface level of the surrounding liquid; especially less than 4 cm, less than 3 cm, less than 2 cm, less than 1 cm, or less than 0.5 cm lower than the surface level of the surrounding liquid. In another embodiment, the stirring being performed substantially without forming a vortex is when the surface area of the liquid is less than 10% greater than the liquid when not stirred; especially less than 9%, less than 8%, less than 7%, less than 6%, less than 5%, less than 4%, less than 3%, less than 2% or less than 1% greater than the liquid when not stirred.

In the present specification and claims, the word 'comprising' and its derivatives including 'comprises' and 'comprise' include each of the stated integers but does not exclude the inclusion of one or more further integers.

As used herein, the term "liquid" comprises free-flowing solutions, for example, aqueous solutions (for example a solution which does not comprise a gelation agent). The term "liquid" also comprises viscous liquids, such as a gel.

The pharmaceutical composition prepared by the method of the first aspect may be in any suitable form. In one embodiment, the composition is in the form of a solution. In another embodiment, the composition is in the form of a gel or cream; especially a gel. The composition may be of any suitable viscosity. In one embodiment, the composition has a viscosity of from 0.01 cPs to 2,500 cPs (0.00001 Pa·s to 2.5 Pa·s) at 20° C.; or from 0.1 cPs to 2,000 cPs (0.0001 Pa·s to 2 Pa·s) at 20° C. In another embodiment, the composition has a viscosity of from 2,500 cPs to 15,000 cPs (2.5 Pa·s to 15 Pa·s) at 20° C., especially from 5,000 cPs to 13,000 cPs (5 Pa·s to 13 Pa s) at 20° C., more especially from 7,000 cPs to 11,000 cPs (7 Pa·s to 11 Pa·s) at 20° C.

While gel forms of the composition may be preferred, the composition may also be in the form of a solution. The gel form may be easier to apply to a subject than a solution form, and have improved adherence to the subject than a solution form. Consequently, the gel form may have improved anesthetic effect. The gel form may also be stable for a longer period of time than the solution form, for example, as it may be more difficult for oxygen or other gases to penetrate the more viscous gel. However, it has previously been difficult to prepare the gel, as biopolymer gelation agents (such as methylcellulose and hydroxypropyl methyl cellulose) are relatively slow to solubilize (taking up to 24 hours) and can dilute oxygen scavengers present in gel, and the time needed to formulate the gel may be not acceptable for an Emergency Department.

The pharmaceutical composition prepared by the method of the first aspect may have any suitable pH. In one embodiment, the pharmaceutical composition prepared by the method of the first aspect has a pH of from 2.5 to 4.5, or from 3 to 4.2, or from 3.5 to 4.0, or about 3.7.

The aqueous liquid stirred in the first aspect may be at least 50% water (by volume), especially at least 60%, or at least 70%, or at least 80% or at least 90% water (by volume). The aqueous liquid stirred in the first aspect may be at least 95% water (by volume). In one embodiment, the aqueous liquid stirred in the first aspect is water. Solvents which may be present in the aqueous solution may be selected from the group consisting of: water, water-miscible solvents and water-immiscible solvents. Exemplary water-miscible solvents may comprise an alcohol (such as methanol, ethanol, propanol, isopropanol or glycerol) and a glycol (such as propylene glycol, polyethylene glycol). Exemplary water-immiscible solvents may comprise an oil, and a fatty acid ester (such as isopropyl myristate). Any such solvents should be selected so as not to increase penetration of the local anesthetic agent or the vasoconstrictive agent into the systemic circulation of a subject (which could affect toxicity). In one embodiment, the aqueous liquid stirred in the first aspect is a deoxygenated aqueous liquid. The aqueous liquid may be deoxygenated by any suitable method, including through use of oxygen scavengers, or sparging the liquid with an inert gas.

The at least one local anesthetic agent may be any number of anesthetic agents. The topical pharmaceutical composition may comprise one, two, three, four or five local anesthetic agents for example. In one embodiment, the pharmaceutical composition comprises one local anesthetic agent. In another embodiment, the pharmaceutical composition comprises two local anesthetic agents.

The at least one local anesthetic agent may be selected from the group consisting of: acetamidoeugenol, alfadolone acetate, alfaxalone, amucaine, amolanone, amylocaine, articaine, benoxinate, benzocaine, betoxycaine, biphenamine, bupivacaine, burethamine, butacaine, butaben, butanilicaine, buthalital, butoxycaine, carticaine, 2-chloroprocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutylp-aminobenzoate, kentamine, leucinocaine mesylate, levoxadrol, lignocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, ropivacaine, salicyl alcohol, tetracaine, thialbarbital, thimylal, thiobutabarbital, thiopental, tolycaine, trimecaine and zolamine and combinations thereof.

In one embodiment, the at least one local anesthetic agent is selected from the group consisting of tetracaine, lignocaine, prilocaine, benzocaine, and combinations thereof. In one embodiment, the at least one local anesthetic agent is lignocaine and tetracaine.

The at least one local anesthetic agent may comprise an amide functional group. Exemplary such local anesthetic agents may be selected from the group consisting of: lignocaine (also known as xylocaine and lidocaine), bupivacaine, prilocaine, articaine, ropivacaine and mepivacaine. The at least one local anesthetic agent may comprise an ester functional group. Exemplary such local anesthetic agents may be selected from the group consisting of: procaine, tetracaine (also known as amethocaine), cocaine, and benzocaine. In general, the ester type may have a faster onset of action due to its more lipophilic nature which allows penetration of the epidermis.

As used herein, the term "local anesthetic agent" refers to an anesthetic agent that when administered topically has a local effect. Some such anesthetic agents may also exhibit a systemic effect when administered by other routes. Such anesthetic agents have specific characteristics which define their clinical use. For example, when compared to bupivacaine, lignocaine has a faster onset of action, but is effective for a shorter period of time.

Any suitable amount of the at least one local anesthetic agent may be present in the pharmaceutical composition. In one embodiment, the total amount of the at least one local anesthetic agent in the composition prepared by the method of the first aspect is from about 0.1 wt % to about 10 wt % of the pharmaceutical composition, especially from about 1 wt % to about 8 wt %, or from about 2 wt % to about 6 wt %, or from about 3 wt % to about 5 wt % of the pharmaceutical composition. In one embodiment, the amount of each of the at least one local anesthetic agent in the composition prepared by the method of the first aspect is from about 0.1 wt % to about 10 wt % of the pharmaceutical composition, especially from about 0.1 wt % to about 8 wt %, or from about 0.2 wt % to about 6 wt %, or from about 0.2 wt % to about 5 wt % of the pharmaceutical composition.

When a local anesthetic agent having an amide functional group (especially lignocaine) is present in the composition, it may be present at from about 1 wt % to about 7 wt % of the composition, or from about 2 wt % to about 6 wt %, or from about 3 wt % to about 5 wt % of the composition, or about 4 wt % of the composition. When a local anesthetic agent having an ester functional group (especially tetracaine) is present in the composition, it may be present at from about 0.01 wt % to about 2 wt %, or from about 0.05 wt % to about 1.5 wt % of the composition, or from about 0.1 wt % to about 1 wt % of the composition, or about 0.5 wt % of the composition. In one embodiment, the amount of the at least one local anesthetic agent in the pharmaceutical composition has a maximum of ±5% variance.

The vasoconstrictive agent may be at least one vasoconstrictive agent, such as two, three or four vasoconstrictive agents. However, in one embodiment the vasoconstrictive agent is one vasoconstrictive agent. The vasoconstrictive agent may be selected from the group consisting of: adrenaline, metaraminol, phenylephrine and norepinephrine, or a combination thereof; especially adrenaline, metaraminol, phenylephrine and norepinephrine. The vasoconstrictive agent may be adrenaline. The vasoconstrictive agent may be an adrenergic sympathomimetic agent. Exemplary adrenergic sympathomimetic agents are adrenaline, metaraminol, phenylephrine and norepinephrine.

Any suitable amount of the vasoconstrictive agent may be present in the pharmaceutical composition. In one embodiment, the total amount of the vasoconstrictive agent in the composition prepared by the method of the first aspect is from about 0.001 wt % to about 0.50 wt % of the composition, especially from about 0.005 wt % to about 0.35 wt %, or from about 0.01 wt % to about 0.25 wt %, or from about 0.05 wt % to about 0.20 wt % of the composition. In one embodiment, the amount of the vasoconstrictive agent in the pharmaceutical composition has a maximum of ±5% variance.

In one embodiment, the at least one local anesthetic agent is lignocaine and tetracaine, and the vasoconstrictive agent is adrenaline. Advantageously, the combination of lignocaine, tetracaine and adrenaline can slow or stop bleeding from a wound while working in 20-30 minutes. The presence of adrenaline may induce vasoconstriction, which slows bleeding whilst simultaneously slowing the removal of the local anesthetic agent and increasing the duration of their effect. For example, topical lignocaine anesthesia without adrenalin may last for around 30-60 min, but topical lignocaine anesthesia with adrenaline may last for around 120-360 minutes (Huether et al). Furthermore, the use of adrenaline to reduce the blood supply at the wound may also reduce the likelihood of tetracaine entering systemic circulation (where it may exhibit toxic effects). Furthermore, the use of adrenaline may cause "blanching" around the wound, which may indicate when the anesthesia has taken effect.

In one embodiment the pharmaceutical composition may further comprise an oxygen scavenger (or antioxidant). The aqueous liquid in the method of the first aspect may comprise an oxygen scavenger (or antioxidant). Consequently, the method of the first aspect may comprise the step of stirring an aqueous liquid comprising at least one local anesthetic agent, a vasoconstrictive agent and an oxygen scavenger (or antioxidant). The presence of an oxygen scavenger may be advantageous, for example to assist in minimizing the concentration or amount of oxygen present in the pharmaceutical composition.

The oxygen scavenger (or antioxidant) may be selected from the group consisting of ascorbic acid, acetyl cysteine, thiourea, a sulfite or a combination thereof. The sulfite may be a metabisulfite (especially sodium metabisulfite).

Any suitable amount of the oxygen scavenger (or antioxidant) may be present in the pharmaceutical composition. In one embodiment, the amount of the oxygen scavenger (or antioxidant) in the composition prepared by the method of the first aspect is from about 0.001 wt % to about 0.50 wt % of the composition, especially from about 0.005 wt % to about 0.35 wt %, or from about 0.01 wt % to about 0.25 wt %, or from about 0.05 wt % to about 0.20 wt %, or about 0.1 wt % of the composition.

The liquid may further comprise a gelation agent. In one embodiment, the liquid further comprises a gelation agent, and the topical pharmaceutical composition is in the form of a gel.

Any suitable gelation agent may be used. In one embodiment, the gelation agent is a hydrophilic gelation agent, especially a hydrophilic polymeric gelation agent. The gelation agent may be a thickening agent. The gelation agent may be a nonliposomal gelation agent, especially a nonliposomal polymeric gelation agent. The gelation agent may be selected from the group consisting of: a starch, cellulose, a cellulose ester, a poloxamer, a carbomer, an acrylate, an acrylate copolymer (such as acrylamide-sodium acrylate copolymer), cetostearyl alcohol, gelatin, an alginate, a pectin, acacia gum, locust bean gum, karaya gum, tragacanth gum, xanthan gum, guar gum and carrageenan, or a combination thereof. In one embodiment, the gelation agent is a cellulosic gelation agent. The gelation agent may be selected from the group consisting of ethyl cellulose, methyl cellulose, hydroxypropylmethyl (hypromellose)cellulose and combinations thereof. The gelation agent may be hydroxypropylmethyl cellulose.

In one embodiment, the gelation agent may have a viscosity of from 1,750 to 8,000 cPs (2.5 Pa·s to 8 Pa·s), or from 2,500 to 6,000 cPs (2.5 Pa·s to 6 Pa·s), or from 3,000 to 5,000 cPs (3 Pa·s to 5 Pa·s) or about 3,000 to 4,000 cPs (4 Pa·s). In one embodiment, the amount of the gelation agent in the composition prepared by the method of the first aspect is from about 0.01 wt % to about 15 wt % of the composition, especially from about 0.1 wt % to about 10 wt %, or from about 0.5 wt % to about 5 wt % of the composition. In one embodiment, the amount of the gelation agent in the composition prepared by the method of the first aspect is from about 0.1 wt % to about 5 wt % of the composition, especially from about 0.5 wt % to about 4 wt %, or from about 1 wt % to about 3.5 wt %, or from about 1.5 wt % to about 3.0 wt %, or from about 2 wt % to about 2.5 wt %, or about 2.25 wt % of the composition. In one embodiment, the ratio of the at least one local anesthetic agent to gelation agent in the pharmaceutical composition may be from about 0.5:1 to about 5:1, or from about 1:1 to 3:1 or about 2:1 or about 1.8:1.

The stirring in the method of the first aspect may be performed in any suitable way. In one embodiment, the stirring is performed with an impeller. The impeller may comprise a blade. The impeller may comprise a shaft connected to the blade. The blade of the impeller may define a plurality of apertures. The plurality of apertures may be evenly distributed. Even distribution of the apertures allows jets to form as the impeller is rotated. The impeller blade may be substantially planar. The impeller blade may define a plurality of substantially rectangular apertures. From about 10% to about 40% of the surface area of the impeller blade may comprise apertures, or from about 15% to about 30%, or from about 20% to about 25% of the surface area of the impeller blade may comprise apertures. Of the area defined by the edges of the impeller blade, from about 10% to about 40% may be apertures (or voids), or from about 15% to about 30%, or from about 20% to about 25% may be apertures (or voids). The impeller blade may define any number of apertures. In one embodiment, the impeller blade defines two apertures. In one embodiment, each said aperture comprises from about 5% to about 20% or from about 10 to about 15% of the total surface area of the impeller blade. The axis about which the impeller blade rotates may be an axis of symmetry. The inventors have advantageously found that an impeller blade with large symmetrically positioned apertures is able to produce a "sweeping and pass through" motion (and thus low shear, allowing stirring substantially without forming a vortex). The impeller may also aid in the dispersion of the gelation agent. The impeller may be rotated at a speed of from 10 rpm to 80 rpm, especially between 20 rpm to 60 rpm, or from 35 to 45 rpm; especially for at least 20 minutes, or at least 60 minutes. The impeller may then be rotated at a speed of from 100 to 300 rpm, or from 120 to 250 rpm, or from 140 to 200 rpm, or from 150 to 180 rpm; especially for at least 30 minutes, or at least 60 minutes. The aqueous solution comprising the at least one local anesthetic agent and the vasoconstrictive agent may be stirred until it is ready for use or packaging.

In one embodiment of the method of the first aspect, the aqueous liquid comprising the at least one local anesthetic agent and a vasoconstrictive agent is stirred at less than 50° C., or less than 40° C., or less than 30° C. In one embodiment of the method of the first aspect, the aqueous liquid comprising the at least one local anesthetic agent and a vasoconstrictive agent is stirred at atmospheric pressure.

In one embodiment of the method of the first aspect, the method comprises combining a first liquid comprising the at least one local anesthetic agent and a second liquid comprising the vasoconstrictive agent to thereby provide the aqueous liquid comprising the at least one local anesthetic agent and the vasoconstrictive agent. In one embodiment, the first liquid and second liquid are each cooled to a temperature of less than about 30° C., especially less than about 25° C., or less than about 20° C. before combining. The step of combining may comprise adding the second liquid into the first liquid. The first liquid may be stirred as described above.

The first liquid may comprise at least 50% water (by volume), especially at least 60%, or at least 70%, or at least 80% or at least 90% water (by volume). The first liquid may be at least 95% water (by volume). In one embodiment, the first liquid is water. Solvents which may be present in the first liquid may be selected from the group consisting of: water, water-miscible solvents and water-immiscible solvents. Exemplary water-miscible solvents may comprise an alcohol (such as methanol, ethanol, propanol, isopropanol or glycerol) and a glycol (such as propylene glycol, polyethylene glycol). Exemplary water-immiscible solvents may comprise an oil, and a fatty acid ester (such as isopropyl myristate). In one embodiment, the first liquid is a deoxygenated liquid. The first liquid may be deoxygenated by any suitable method, including through use of oxygen scavengers, or sparging the liquid with an inert gas.

The second liquid may comprise at least 50% water (by volume), especially at least 60%, or at least 70%, or at least 80% or at least 90% water (by volume). The second liquid may be at least 95% water (by volume). In one embodiment, the second liquid is water. Solvents which may be present in the second liquid may be selected from the group consisting of: water, water-miscible solvents and water-immiscible solvents. Exemplary water-miscible solvents may comprise an alcohol (such as methanol, ethanol, propanol, isopropanol or glycerol) and a glycol (such as propylene glycol, polyethylene glycol). Exemplary water-immiscible solvents may comprise an oil, and a fatty acid ester (such as isopropyl myristate). In one embodiment, the second liquid is a deoxygenated liquid. The second liquid may be deoxygenated by any suitable method, including through use of oxygen scavengers, or sparging the liquid with an inert gas.

In one embodiment, the first liquid may comprise a gelation agent. The gelation agent may be as described above.

In another embodiment, the method of the first aspect may further comprises preparing the first liquid by dry blending the at least one local anesthetic agent and the gelation agent, and then adding the dry blend to a stirred liquid, wherein the liquid is stirred substantially without forming a vortex and under an inert gas. In one embodiment, the ratio of the at least one local anesthetic agent to gelation agent in the first liquid may be from about 0.5:1 to about 5:1, or from about 1:1 to 3:1 or about 2:1 or about 1.8:1. The step of adding the dry blend to a stirred liquid may be performed at any suitable temperature. In one embodiment, the temperature is at least 50° C., or at least 60° C., or at least 70° C., or at least 80° C. or at least 85° C. In one embodiment, the temperature is less than 100° C., or less than 95° C., or less than 90° C. The step of adding the dry blend may be performed slowly, for example over greater than 10 minutes, especially greater than 15 minutes. The stirred liquid may be stirred in any suitable way, especially by the impeller described above. The impeller may be rotated at a speed of from 50 rpm to 500 rpm, especially between 100 rpm to 350 rpm, or from 150 to 250 rpm. The inert gas may be as described above. The inert gas may be nitrogen. The step of dry blending may advantageously disperse the gelation agent and assist in dissolving the gelation agent. The first liquid may be maintained at a pH of less than 9, especially less than 8, 7, 6, 5 or 4. In one embodiment, the first liquid is heated to greater than 85° C. and then cooled to from 25 to 35° C. (especially about 30° C.) before standing for at least 10 hours.

The stirred liquid discussed in the preceding paragraph may be under an inert gas in any suitable way. For example, the step of stirring may comprise flowing the inert gas over the surface of the aqueous liquid. A suitable rate of flow of the inert gas may be selected by a skilled person. In another embodiment, the step of stirring may comprise positioning the liquid in a closed container and displacing gas in the closed container with the inert gas. For the avoidance of doubt, in a closed container there may be gaps, for example in the lid, where inert gas and residual oxygen may escape. In one embodiment, the flow rate of inert gas is from 0.5% to 100% of the container volume per minute, especially from 0.5% to 80% or from 0.5% to 60% or from 0.5% to 40% or from 0.5% to 30% or from 1% to 20% or from 2% to 10% of the container volume per minute.

After the first liquid is prepared it may be cooled before the first liquid and the second liquid are combined. In one embodiment, the first liquid is cooled to a temperature of less than about 40° C., especially less than about 35° C., or less than 30° C. In one embodiment, the first liquid is cooled to a temperature of about 20-25° C. In one embodiment, the first liquid is cooled to a temperature of from 10° C. to 35° C., especially from 15° C. to 35° C. or from 20° C. to 30° C. The cooling may be gradual. The cooling may be without use of a cooling device. After the first liquid is cooled it may be allowed to stand for at least 10 hours, especially at least 15 hours, or at least 16 hours. Advantageously, gradual cooling followed by standing may allow for complete and even hydration of the gelation agent (such as hydroxypropylmethyl cellulose (HPMC)). The first liquid may remain under an inert gas during cooling and standing.

In one embodiment, the method of the first aspect further comprises preparing the second liquid by adding the vasoconstrictive agent to a stirred liquid. In another embodiment, the method of the first aspect further comprises preparing the second liquid by adding an oxygen scavenger to a stirred liquid, and then adding the vasoconstrictive agent to the stirred liquid, wherein the liquid is stirred substantially without forming a vortex and under an inert gas. Features of these embodiments may be as described above. In particular, the oxygen scavenger, and inert gas may be as described above. The stirred liquid may be stirred in any suitable way, especially by the impeller described above. The impeller may be rotated at a speed of from 10 rpm to 80 rpm, especially between 20 rpm to 60 rpm, or from 35 to 45 rpm. The inert gas may be as described above. The inert gas may be nitrogen.

The stirred liquid discussed in the preceding paragraph may be under an inert gas in any suitable way. For example, the step of stirring may comprise flowing the inert gas over the surface of the aqueous liquid. A suitable rate of flow of the inert gas may be selected by a skilled person. In another embodiment, the step of stirring may comprise positioning the liquid in a closed container and displacing gas in the closed container with the inert gas. For the avoidance of doubt, in a closed container there may be gaps, for example in the lid, where inert gas and residual oxygen may escape. In one embodiment, the flow rate of inert gas is from 0.5% to 100% of the container volume per minute, especially from 0.5% to 80% or from 0.5% to 60% or from 0.5% to 40% or from 0.5% to 30% or from 1% to 20% or from 2% to 10% of the container volume per minute.

Accordingly, in one embodiment, the present invention provides a method of preparing a topical pharmaceutical composition, the method comprising:

(i) Preparing a first liquid by dry blending at least one local anesthetic agent and a gelation agent, and then adding the dry blend to a stirred aqueous liquid, wherein the liquid is stirred substantially without forming a vortex and under an inert gas;

(ii) Preparing a second liquid by adding an oxygen scavenger and a vasoconstrictive agent to a stirred aqueous liquid, wherein the liquid is stirred substantially without forming a vortex and under an inert gas; and (iii) Combining and stirring the first and second liquids together, wherein the stirring is performed substantially without forming a vortex and under an inert gas.

Features of this embodiment may be as described above. In one embodiment, the at least one anesthetic agent is lignocaine and tetracaine; the at least one vasoconstrictive agent is adrenaline; and the gelation agent is hydroxypropylmethyl cellulose.

In one embodiment, the liquids used in the method (especially the second liquid, and the aqueous liquid comprising the at least one local anesthetic agent and the vasoconstrictive agent) are protected from light, especially UV light.

The method of the first aspect may further comprise the step of filling containers with the aqueous liquid comprising the at least one local anesthetic agent and the vasoconstrictive agent. In one embodiment, during filling the aqueous liquid is at a temperature of from about 20° C. to about 45° C., especially from about 25° C. to about 40° C., or from about 30° C. to about 40° C., or at about 35° C. to 37° C. or at about 35° C. to 36° C. The inventors have advantageously found that this filling temperature is effective for pharmaceutical compositions which comprise a gelation agent, especially wherein the gelation agent is HPMC. At such a filling temperature the containers may be filled quickly which reduces the likelihood of oxygen ingress. In one embodiment, during filling the container being filled is under an inert gas, especially the headspace of the container is under an inert gas, especially overlayed with an inert gas. The inert gas may be as described above. The inert gas may be nitrogen. The headspace of the filled container may comprise less than 6% of oxygen, or less than 5% of oxygen, or less than 4% of oxygen or less than 3% of oxygen (by volume).

In one embodiment the container being filled is photoresistant, or does not allow entry of light. In one embodiment, the container being filled is coloured amber. In one embodiment, the container is an ampoule, vial or syringe.

The method of the first aspect may include the step of sealing the container.

The filled and sealed container may be sterilized. The filled and sealed container may be autoclaved. A typical autoclave procedure involves a temperature of 121° C. for 20 minutes.

In one embodiment, the pharmaceutical composition prepared by the first aspect may be sterile. The pharmaceutical composition prepared by the first aspect may be stable at room temperature (or at from 20 to 30° C., especially about 25° C.) for at least 12 months, especially at least 18 months or at least 24 months. The pharmaceutical composition of the first aspect may comprise no preservatives. The pharmaceutical composition of the first aspect may comprise no penetrating agents.

The topical pharmaceutical composition may be suitable for application to any part of a subject, including on skin (including broken skin) and mucosa. The term "skin" may include the epidermis of a subject. The topical pharmaceutical composition may be suitable for use on mucosal damage, such as mucosal inflammation, abrasions, ulcerations, lesions, trauma and incisions.

As used herein, the terms "subject" or "individual" or "patient" may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human.

According to a second aspect, the present invention provides a topical pharmaceutical composition prepared by the method of the first aspect. Features of the topical pharmaceutical composition of the second aspect may be as described for the first aspect.

According to a third aspect, the present invention provides a topical pharmaceutical composition comprising at least one local anesthetic agent and a vasoconstrictive agent in an aqueous liquid, wherein the liquid is a deoxygenated liquid.

According to a fourth aspect, the present invention provides a topical pharmaceutical composition comprising at least one local anesthetic agent and a vasoconstrictive agent in an aqueous liquid, wherein the liquid comprises less than 5 ppm oxygen.

In one embodiment of the fourth aspect, the liquid comprises less than 4 ppm, less than 3 ppm, less than 2 ppm, less than 1 ppm or less than 0.5 ppm oxygen.

Features of the third and fourth aspects of the present invention may be as described for the first and second aspects of the present invention.

In one embodiment of the third and fourth aspects, the at least one local anesthetic agent may be lignocaine and tetracaine. In one embodiment of the third and fourth aspects, the vasoconstrictive agent is adrenaline. The liquid of the third or fourth aspects may be water. The pharmaceutical composition of the third and fourth aspects may further comprise an oxygen scavenger (or antioxidant), especially a sulfite, more especially metabisulfite. The pharmaceutical composition of the third and fourth aspects may be in the form of a solution or a gel, especially a gel. The pharmaceutical composition of the third and fourth aspects may comprise a gelation agent; especially hydroxypropylmethyl cellulose.

According to a fifth aspect, the present invention provides a method of reducing blood loss and pain at a topical area of a subject, comprising administering the pharmaceutical composition of the first aspect to the subject (or of the second, third or fourth aspects to the subject), or a topical pharmaceutical composition prepared by the method of the first aspect.

According to a sixth aspect, the present invention provides a use of at least one local anesthetic agent and a vasoconstrictive agent in the manufacture of a topical pharmaceutical composition for the treatment of blood loss and pain, wherein the pharmaceutical composition is as defined by the second, third or fourth aspect.

According to a seventh aspect, the present invention provides a method of treating blood loss and pain, comprising topically administering to a subject in need thereof the pharmaceutical composition of the second, third or fourth aspect.

According to an eighth aspect, the present invention provides the topical pharmaceutical composition of the second, third or fourth aspect, for use in treating blood loss and pain.

Features of the second to eighth aspects may be as described for the first aspect. In one embodiment of the fifth to eighth aspects of the present invention, the pharmaceutical composition is applied to broken skin of the subject.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Examples of the invention will now be described by way of example with reference to the accompanying Figures, in which.

Figure 1:
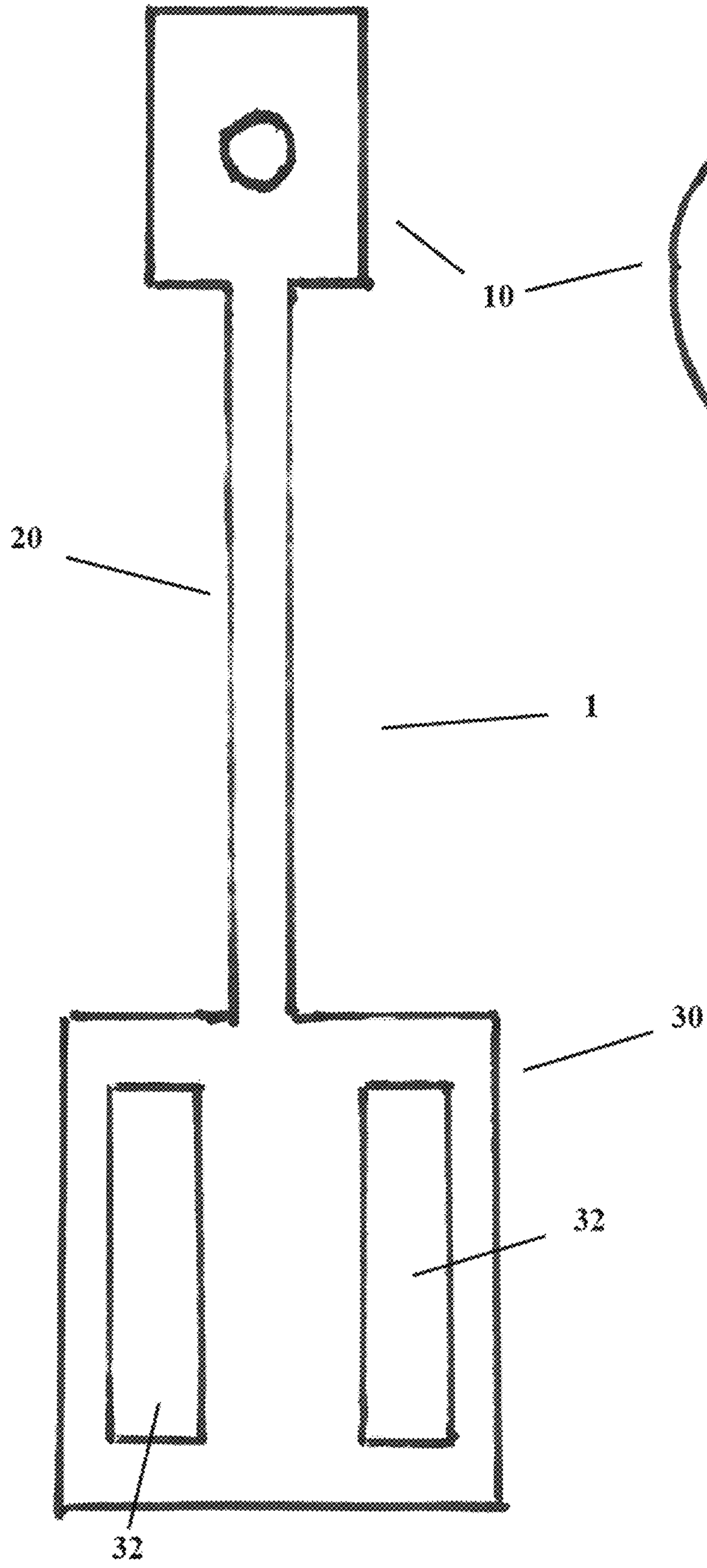
FIG. 1 provides a side view of an impeller used in the method of an embodiment of the invention.

Preferred features, embodiments and variations of the invention may be discerned from the following Examples which provides sufficient information for those skilled in the art to perform the invention. The following Examples are not to be regarded as limiting the scope of the preceding Summary of the Invention in any way.

EXAMPLES

The below Examples relate to a pharmaceutical composition in which the at least one local anesthetic agent is lignocaine and tetracaine, the gelation agent is HPMC, and the vasoconstrictive agent is adrenaline. However, other local anesthetic agents, gelation agents, and vasoconstrictive agents may be used.

Example 1—Selection of Gelation Agent and Concentration

While any of a large number of gelling agents may be used, the most common gelling agent of choice is hydroxypropyl methylcellulose. This is a well-known and widely available commercial coating and gelling agent and excipient that is typically easier to dissolve than methyl celluloses. A wide range of grades are available and depending on the concentration will give differing viscosities. The HPMC grades may vary (based on a 2% concentration) from a low viscosity of 3 mPa (nominal 1-5 mPa or cPs) to 100,000 mPa (nominal viscosity between 150,000-280,000 mPa or cPs) (average Mwt 1,200,000). The choice of grade and the viscosity depend on trials. It was determined that a viscosity at 2.25% of an average Mwt 400,000 grade HPMC gave a satisfactory product for application and adherence of 4,000 mPa (nominal between 2,600 to 5,000 mPa or cPs).

Experimentally the 4,000 mPa grade was examined from 0.5% to 5% aiming to provide a workable, pourable and dissolvable gel that is sufficient to pour from an amber glass vial and yet viscous enough to apply to and into a wound without undue run off that may make it difficult to determine the dose given. This was chosen to eliminate the need for use of cotton balls or swabs making it quicker and safer to apply.

Experiments were conducted with a medical team at a teaching hospital on different wounds (abrasions to lacerations to deep cuts and so on) on pig trotters, examining applicability including into deep wounds and also the ability to suture the wounds without loss of the gel from it oozing away. A final concentration of an average of 3,000-4,000 mPa HPMC of 2.25% was found to be the most appropriate (see Table 1).

This concentration was chosen to develop and discover the best way to dissolve the HPMC and later add the drugs and metabisulfite while reducing oxygen intrusion.

TABLE 1

Gel thickness Level and Pour Ability and Adherence into a Wound or Laceration

| Gelation Level | Pour ability(+) | Application(*) | Adherence |
|---|---|---|---|
| 0.1% | ++ | * | + |
| 0.25% | ++ | * | + |
| 0.5% | ++ | ** | + |
| 1.0% | +++ | ** | ++ |
| 1.5% | +++ | *** | ++ |
| 2.0% | ++++ | ***** | +++ |
| 2.25% | +++++ | ***** | ++++ |
| 3.0% | ++ | *** | ++++ |
| 4.0% | + | ** | +++++ |
| 5.0% | + | * | +++++ |

Further all the factors and steps/procedures in the manufacture were examined.

Example 2—Preparation of Pharmaceutical Composition

A pharmaceutical composition with the parameters set out in Table 2 was prepared according to the method of the present invention.

TABLE 2

Formulation & Release Specifications for a Room Temperature (25° C.) Stable LAT (Autoclaved at 121° C. for 20 minutes)

| Substance | Amount per mL at manufacture | Acceptance criteria release | Variance limits |
|---|---|---|---|
| Lignocaine hydrochloride monohydrate (anhydrous) | 40.0 mg/mL | 38.0-41.5 mg/mL (+/−5%) | (+/−5%) |

TABLE 2-continued

Formulation & Release Specifications for a Room Temperature (25° C.) Stable LAT (Autoclaved at 121° C. for 20 minutes)

| Substance | Amount per mL at manufacture | Acceptance criteria release | Variance limits |
|---|---|---|---|
| Amethocaine (Tetracaine) hydrochloride | 5.0 mg/mL | 4.75-5.25 mg/mL (+/−5%) | (+/−5%) |
| Adrenaline acid tartrate | 1.8 mg/mL | 1.71-1.98 mg/mL (+/−5%) | (+/−5%) |
| Sodium metabisulphite | 1.0 mg/mL | Not assayed | NA |
| Hydroxypropylmethylcellulose (HPMC) | 22.5 mg/mL | Not assayed | NA |
| Water for Injection | qs | Not assayed | NA |

All steps outlined below were protected from light.

Preparation of First Liquid

Lignocaine, tetracaine and HPMC were vigorously blended in a ratio of 2 parts lignocaine and tetracaine:1 part HPMC.

Water for injection (WFI) was added to a container which had a low head space and a closefitting lid to reduce ingress of oxygen and create a "fixed head space volume". Over the headspace was provided a nitrogen overlay. The WFI was also sparged with the inert gas (nitrogen).

The WFI was heated to greater than 85-90° C. and then the dry blend was slowly added over >15 minutes (the temperature thickened HPMC reduces the ingress of oxygen to the gel mixture).

Figure 2:
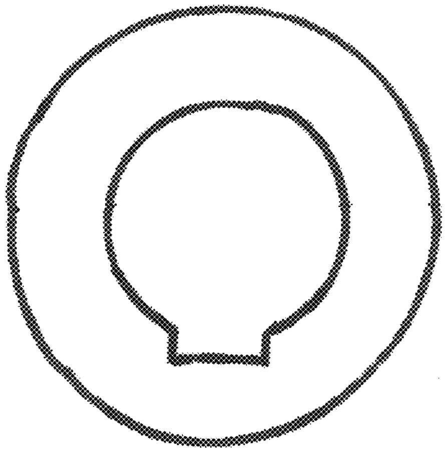
FIG. 2 provides a top view of the top portion of the impeller of FIG. 1.

During this addition step, the impeller 1 illustrated in FIGS. 1 and 2 was used to stir the solution. The impeller comprises a head 10, a shaft 20, and a blade 30. As illustrated in FIG. 1, the blade 30 includes two apertures 32. Each aperture 32 is substantially rectangular and is approximately 25 mm wide and approximately 100 mm high. By comparison the blade 30 is about 150 mm high and about 150 mm wide and is substantially planar. The shaft 20 and head 10 together have a length of 850 mm, and the head 10 a length of 99.9 mm and a width of 50 mm. The apertures 32 in the blade 30 are evenly distributed, and are symmetrically positioned. The impeller blade has an axis of symmetry which is co-axial with the axis of rotation with of the impeller 1. The inventors have advantageously found that an impeller blade with large symmetrically positioned apertures is able to produce a "sweeping and pass through" motion (and thus low shear, allowing stirring substantially without forming a vortex).

The first liquid is stirred with impeller 1 at a rate of between 150-250 rpm under a nitrogen gas until all particles are wetted.

The first liquid was then gradually allowed to cool to a temperature of below 30° C. until hydration of the HPMC was complete. This step was performed without use of any cooling device, and this allows natural hydration of the HPMC within the mixture.

The first liquid was next held (or left to stand) for a period of between 16-24 hours to allow complete and slow gelation and allow natural (not aided) cooling and thus the complete an even hydration of the HPMC. This provides a reproducible control of viscosity. The final the temperature of the first liquid was allowed to slowly drop to approximately 30° C. or less. During this time the nitrogen head space in the bulk vessel was maintained.

Preparation of Second Liquid

A small volume of WFI was filled into a vessel or container (<10 litres) and sparged with nitrogen for no less than 30 minutes with a nitrogen flow rate of 6 sLpm. The bisulfite was added to this solution and the mixture stirred at 35-45 rpm, using impeller 1, until a clear solution was obtained.

Adrenaline was added to the solution with the same nitrogen and stir rate parameters until it was dissolved.

Combining the First and Second Liquids

The first and second liquids were allowed to cool to <20° C.

The second liquid was then added to the first liquid, and additional water was added to bring up to the correct volume. The mixture was stirred for a minimum of 20 minutes at 35-45 rpm, preferably 60 minutes, (using impeller 1) without shear and vortexes, and whilst being overlayed with nitrogen at a rate of 1.5 sLpm. The speed of stirring was then raised to 150-180 rpm (avoiding shear and vortex formation) for 60 minutes.

Additional WFI was added to the container if the bulk volume was too low. The mixture was then stirred at 150-180 rpm until the mixture was ready to be used to fill containers for packaging. If the mixture was not immediately used for a fill operation, the bulk solution was constantly stirred at 150-180 rpm keeping a tight lid on the vessel and filling the headspace with nitrogen. To prevent oxygen ingress no more than 48 hours was allowed to pass between formation of the pharmaceutical composition and filling the containers.

Example 3—Packaging Pharmaceutical Composition

Extractable Volume & Oxygen Ingress/Infiltration During Filling

Oxygen ingress during the filling and the oxygen level in the vial headspace are potential sources of oxygen in the finished and packaged LAT product which affect stability.

It was found that the temperature of the actual vial filling was important since from a physical viewpoint, in automated filling, peristaltic pumps are used and as the HPMC is a thixotropic agent it has the potential to make peristalsis very difficult and fill volumes variable due to viscosity variations related to even small temperature changes in the bulk solution.

Further, an advantage of a faster or minimum filling rate is that the faster the fill rate the less likelihood of oxygen ingress into the bulk solution due to its hold time although this is balanced against the potential loss of inert gas over capping becoming variable and not evenly excluding oxygen.

It was found that the viscosity changed significantly depending on the temperature that the bulk gel was held at during the fill process. Optimally for speed the fill temperature was set at 36° C. and a range from 30-45° C., especially 35-36° C. The slightly elevated temperatures did not affect the bulk solution but did help reduce oxygen ingress.

Control of Oxygen in Vial Head Space

Using two different methods to measure oxygen in vial head space it was found that it was advantageous to start with as low a level in the head space as possible. It was also determined that the oxygen in the space (5 mL) declined over the first 28 days by as much as 59% which was attributed to absorption/equilibration into the liquid and potentially the oxygen reacting with the metabisulphite and the active agents.

Since the metabisulphite is a fixed quantity within the pharmaceutical composition and it is destroyed by the reaction with oxygen, the importance of measuring the oxygen level in the container headspace during filling is fundamental to obtaining a long-term stability. It was found that this should be less than 5% $O_2$, preferably less than 4% $O_2$ or preferably less than 3% $O_2$.

Hydration of the Gelation Agent (HPMC or Hypromellose)

HPMC powder dissolves by swelling and subsequent hydration. As such, a very real danger is the presence of undissolved "clear beads" or an incomplete "lumpy" solution of HPMC caused when only part of the powder dissolves leaving incomplete wetting of individual powder particles causing the remainder to form a gelatinous membrane shielding the residual powder from complete hydration. The manufacturer's hydration times are quite long at differing pH's below 8 ranging for surface treated HPMC, from approximately 100 minutes at pH 7 to approximately 400 minutes at pH 3 (Dupont Technical Handbook, 2002). These times are not practicable for pharmaceutical manufacture. The longer the hydration time the greater the likelihood of oxygen entrapment.

Dissolution techniques that are commonly used include agitation by high speed and shear mixing which has the potential to create vortexes and thus suck oxygen into the gel solution and trap it and as well, excess agitation may break down the gel structure and alter its strength and texture. Mixing with high salt concentrations can be used but is not appropriate in the pharmaceutical compositions according to the present invention. Temperature alone is not a sufficient way to resolve this as HPMC is less soluble at higher temperatures.

In this LAT manufacturing process, dispersion of the dry powders of HPMC into the lignocaine and tetracaine dry powder was utilized to initially separate the HPMC powder particles to allow greater water to HPMC surface area contact ratio as is recommended by the manufacturer (Dupont Nutrition and Biosciences 2020). However, the manufacturer states that the minimum mixing ratio of dry powder ingredients to HPMC powder must fall into the range 7:1 to 3:1 (Dupont Nutrition and Biosciences 2020). In contrast, the inventors found that a ratio of 2:1 (the dry powders being lignocaine plus tetracaine mixed to HPMC) may be utilized to obtain the HPMC particle dispersion in this pharmaceutical composition. This is outside the manufacturer's specifications and recommendations.

Gel agent mixing is even more of an issue with methylcellulose. The inventors found that without heat the dissolution process is very slow and difficult to monitor. Addition of a base to raise the pH to 9 or above causes rapid dissolution but given the low stability of the drugs in this formulation at high pH this is not an appropriate solution.

The inventors determined that heat is necessary for the mixing and dissolution of the HPMC and also to maintain a constant viscosity during filling and to allow the fill rate to be maintained at a commercial level for large scale processes. This is important as HPMC becomes less viscous at certain temperatures and more viscous at others making it difficult to control a constant and reproducible fill volume on automated filling apparatus due to viscosity variations. The inventors found that the optimum filling temperature of bulk LAT in this pharmaceutical composition was 35-37° C.

Low Oxygen Infiltration and Stirring of the Formulation

In trials of many stirrers the inventors found that they could too easily produce shear and vortexes sucking oxygen into the mixture. The inventors developed a specific and dedicated low shear impeller 1 designed to stir highly viscous solutions and gels (FIG. 1-2). This impeller has a paddle shape that produces a "sweeping and pass through" motion (and thus low shear). The impeller blade 30 or paddle is perforated with evenly distributed large spaces (apertures 32) stopping jets forming as the impeller is rotated. It also aids in the dispersion of the HPMC.

Filling Process

Aside from the oxygen ingress the extractable volume from each vial has the potential to vary considerably depending on temperature as well the viscosity of the gel. Minor changes in temperature can change the viscosity and thus the filling rate and fill volume, as illustrated in Table 3.

TABLE 3

Viscosity of a Gel Solution Varies with Temperature

| | Temperature (° C.) | | | |
|---|---|---|---|---|
| | 18 | 23 | 28 | 33 |
| Viscosity (cPs) | 9880 | 7840 | 6260 | 5200 |

The inventors determined that a reasonable fill rate based on the 2.25% HPMC gel was >10 vials per minute and less than 50 vials per minute. The upper limit was set due to the likelihood of the faster rate reducing the effectiveness of the inert nitrogen overlay in the vials (i.e. incomplete gassing or loss of nitrogen due to machine speed).

The inventors discovered that another advantage of the slightly elevated filling temperature (range 30-45° C.) for the 2.25% HPMC gel was that the fill volumes were able to be maintained close to the 4 or 5 mL level in each vial (7 mL vials filled to 4 or 5 mL) based on a fill rate of 32 vials/minute. This is acceptable in an industrial process.

Viscosity

Many grades of HPMC are available and it is known that there are viscosity changes following autoclaving. Following testing related to determining the best temperature to hold the gel at in bulk prior to filling was 30-45° C. A release limit (post autoclaving) for the final product was set at 2500-8000 cPs based on USP test methods. This provided a product that was pourable while at the same time it was thickened sufficiently to hold to a wound or laceration.

Further in trial work with artificially damaged and lacerated pig trotters the best gel level or thickness was examined that provided a pourable gel but one which was still viscous enough to stay in and adhere to a wound to allow it to be sutured. The results showed that the 2.25% level met these criteria (Table 4).

The final viscosity specification for an optimum gel LAT product was a 2.25% or a viscosity between 2500-8000 cPs.

TABLE 4

| Filling Trial Based on a Two head Automated Filling Machine (Bosch) Operating at 32 Vials per Minute & a Bulk Gel Solution Temperature of 35-37° C. Net fill weights (g) in a sample of vials were: | | |
|---|---|---|
| | 4.62 | 4.62 |
| | 4.77 | 4.76 |
| | 4.99 | 4.96 |
| | 5.19 | 4.58 |
| | 5.10 | 4.70 |
| | 4.90 | 5.11 |
| | 5.03 | 4.86 |
| | 4.86 | 4.63 |
| | 4.81 | 4.88 |
| | 4.80 | 5.05 |
| | 4.991 | 4.67 |
| | 4.77 | 5.44 |
| | 4.60 | 4.70 |
| | 4.79 | 4.97 |
| | 4.93 | 4.56 |
| | 4.96 | 4.55 |
| Average | 4.88 | 4.82 |
| St Dev | 0.16 | 0.24 |
| RSD | 3.3% | 5.1% |

Filling Process—Fill to Amber Vials

Optimally for speed the fill temperature of the bulk gel is 36° C. and a range from 30-45° C. Optimally this is 35-36° C. The slightly elevated temperatures did not affect the bulk solution but does help reduce oxygen ingress.

Example 4—Stability of Pharmaceutical Composition

The pharmaceutical composition made by the method outlined in Examples 1 and 2 had the specifications set out in Tables 5 and 6. Utilising this formulation and method of manufacture in multiple batches of greater than 50 litres bulk, this method of manufacture met the release criteria (see Tables 5 and 6) and importantly all drug ingredients met a +/−5% variance which has not been achieved by any other group in a sterile LAT product. Furthermore, the LAT was found to maintain stability for 24 months (Table 6). This demonstrates the stability at 25° C. over the period of 24 months.

TABLE 5

| Extra Release Specifications for the LAT Held at Room Temperature (25° C.) | |
|---|---|
| pH | 3.0-4.2 |
| Viscosity | 1750-8000 cPs |

TABLE 6

Example of Stability of LAT Formulation at 25° C./60% RH Over 24 Months

| | | Months | | | | | | |
|---|---|---|---|---|---|---|---|---|
| Assay | Specification | 0 | 3 | 6 | 9 | 12 | 18 | 24 |
| Lignocaine HCl (mg/mL) | Target: 4.00 mg/mL Range: 38.0-42.0 mg/mL +/−5% | 38.7 | 38.7 | 38.0 | 39.0 | 39.1 | 38.7 | 39.4 |
| Tetracaine HCl (mg/mL) | Target: 5.00 mg/mL Range: 4.75-5.25 mg/mL +/−5% | 4.98 | 4.91 | 4.83 | 4.94 | 4.76 | 4.87 | 4.89 |
| Adrenaline Bitartrate (mg/mL) | Target: 1.80 mg/mL Range: 1.71-1.89 mg/ml +/−5% | 1.77 | 1.71 | 1.84 | 1.75 | 1.80 | 1.75 | 1.70 |
| Viscosity | 1,750-8,000 cPs | 3070 cPs | 3350 cPs | 2660 cPs | 3000 cPs | 2280 cPs | 2560 cPs | 2000 cPs |
| pH | 3.0-4.2 | 3.6 | 3.6 | 3.9 | 3.6 | 3.6 | 3.5 | 3.5 |

Filling should be set between 20-50 vials per minute to reduce oxygen ingress time of the bulk, preferably 30 vials per minute.

During filling the headspace in the amber vials or syringes should be overlayed with nitrogen to optimally obtain 3-4% of oxygen, preferably <4% of oxygen, or more preferably <3% of oxygen, (it was found that the oxygen concentration in a vial head space declines over the first 28 days due to reaction with the metabisulphite in the liquid, but as this is a fixed amount it demonstrates the importance of starting the head space oxygen as low as possible to obtain a longer term stability).

The vials may be autoclaved with a normal cycle usually 121° C. for 20 minutes.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

Advantages of a Preferred Embodiment

A topical pharmaceutical composition prepared according to a preferred embodiment of the method of the first aspect of the invention, in which the at least one local anesthetic agent is lignocaine and tetracaine, and the vasoconstrictive agent is adrenaline, and the pharmaceutical composition is a gel (especially hydroxypropylmethyl cellulose), has advantages including it is:

- Capable of reducing bleeding and providing pain relief at a wound for 2-4 hours after application, without systemic absorption;
- Sterile;
- Does not need to comprise preservatives or penetrating agents;
- Stable at room temperature for up to 24 months;
- In gel form and is convenient for use, for example, in Emergency Departments, in a ready-to-use formulation; and
- Manufacturable with reproducible control over the amounts of the active agents (±5% variance).

REFERENCES

Australian National Coordinating Committee on Therapeutic Goods (NCCTG) 2008 *"A Discussion Paper on Regulation of Extemporaneously Prepared Medicines in Non-Hospital Pharmacies"*

S. Berkman, J. MacGregor, T. Alster 2012 Expert Opin. Drug Saf 11(3) "*Adverse effects of topical anaesthetics for dermatologic procedures"*

Dupont Nutrition and Biosciences 2020. *"Chemistry of Methocel™ Cellulose Ethers—A technical Review"*

Dupont Technical Handbook. 2002 *"Methocel™ Cellulose Ethers—Technical Handbook*

J. Gudeman, M. Jozwiakowski, et al 2013. Drugs R. D. "*Potential Risks of Pharmacy Compounding"*

B. W. Fry, A. E. Ciarlone. 1980b *J.Dent.Res.* 59. *"Storage at body temperatures alters concentration of vasoconstrictors in local anaesthetics"*

M. J. Huether, C. H. Weinberger, D. G. Brodland "*Local Anesthetics" in "Injectable and Mucosal Routes of Drug Administration" Part IX* 56

R. Kennedy, J. Luhmann J. *Pharmacological management of pain and anxiety during emergency procedures in children. Pediatric Drugs.* 2001; 3(5):337-354.

D. L. Palazzolo, S. K. Quadri, 1990 J. Chromat. 518 *"Optimal conditions for long term storage of biogenic amines for subsequent analysis by column chromatography with electrochemical detection"*

Wolf, G. Scherbel 2011. *Krankenhauspharmazie* 32 *"Adrenalin and nor adrenalininverddunnungen"*

The invention claimed is:

1. A method of preparing a topical pharmaceutical composition, the method comprising stirring an aqueous liquid comprising at least one local anesthetic agent and a vasoconstrictive agent, wherein the stirring is performed substantially without forming a vortex and under an inert gas.

2. The method according to claim 1, wherein the method comprises combining a first liquid comprising the at least one local anesthetic agent and a second liquid comprising the vasoconstrictive agent to thereby provide the aqueous liquid comprising the at least one local anesthetic agent and the vasoconstrictive agent.

3. The method of claim 2, wherein the method further comprises preparing the second liquid by adding an oxygen scavenger to a stirred liquid, and then adding the vasoconstrictive agent to the stirred liquid, wherein the liquid is stirred substantially without forming a vortex and under an inert gas.

4. The method of claim 3, wherein the oxygen scavenger is metabisulfite.

5. The method of claim 1, wherein the vasoconstrictive agent is selected from the group consisting of: adrenaline, metaraminol, phenylephrine and norepinephrine.

6. The method of claim 5, wherein the vasoconstrictive agent is adrenaline.

7. The method of claim 1, wherein the liquid further comprises a gelation agent, and the topical pharmaceutical composition is in the form of a gel.

8. The method of claim 2, wherein the first liquid further comprises a gelation agent.

9. The method of claim 8, wherein the method further comprises preparing the first liquid by dry blending the at least one local anesthetic agent and the gelation agent, and then adding the dry blend to a stirred liquid, wherein the liquid is stirred substantially without forming a vortex and under an inert gas.

10. The method of claim 8, wherein the gelation agent is selected from the group consisting of: a starch, cellulose, a cellulose ester, a poloxamer, a carbomer, an acrylate, an acrylate copolymer, cetostearyl alcohol, gelatin, an alginate, a pectin, acacia gum, locust bean gum, karaya gum, tragacanth gum, xanthan gum, guar gum and carrageenan.

11. The method of claim 10, wherein the gelation agent is hydroxypropylmethyl cellulose.

12. The method of claim 1, wherein the at least one local anesthetic agent is selected from the group consisting of: acetamidoeugenol, alfadolone acetate, alfaxalone, amucaine, amolanone, amylocaine, articaine, benoxinate, benzocaine, betoxycaine, biphenamine, bupivacaine, burethamine, butacaine, butaben, butanilicaine, buthalital, butoxycaine, carticaine, 2-chloroprocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutylp-aminobenzoate, kentamine, leucinocaine mesylate, levoxadrol, lignocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, ropivacaine, salicyl alcohol, tetracaine, thialbarbital, thimylal, thiobutabarbital, thiopental, tolycaine, trimecaine and zolamine and combinations thereof.

13. The method of claim 1, wherein the at least one local anesthetic agent is two anesthetic agents.

14. The method of claim 13, wherein the at least one local anesthetic agent is lignocaine and tetracaine.

15. A method of preparing a topical pharmaceutical composition, the method comprising:

(i) Preparing a first liquid by dry blending at least one local anesthetic agent and a gelation agent, and then adding the dry blend to a stirred aqueous liquid, wherein the liquid is stirred substantially without forming a vortex and under an inert gas;

(ii) Preparing a second liquid by adding an oxygen scavenger and a vasoconstrictive agent to a stirred aqueous liquid, wherein the liquid is stirred substantially without forming a vortex and under an inert gas; and (iii) Combining and stirring the first and second liquids together, wherein the stirring is performed substantially without forming a vortex and under an inert gas.

16. The method of claim 15, wherein in step (i) the first liquid is heated to greater than 85° C. and then cooled to from 25 to 35° C. before standing for at least 10 hours.

17. The method of claim 15, wherein in step (iii) the first and second liquids are cooled to less than about 30° C. before being combined.

18. The method of claim 15, wherein the at least one anesthetic agent is lignocaine and tetracaine; wherein the at least one vasoconstrictive agent is adrenaline; and wherein the gelation agent is hydroxypropylmethyl cellulose.

* * * * *